United States Patent [19]
Yu et al.

[11] Patent Number: 6,134,944
[45] Date of Patent: Oct. 24, 2000

[54] SYSTEM AND METHOD FOR PRECONCENTRATING, IDENTIFYING, AND QUANTIFYING CHEMICAL AND BIOLOGICAL SUBSTANCES

[75] Inventors: Conrad M. Yu, Antioch; Jackson C. Koo, San Ramon, both of Calif.

[73] Assignee: The Regents of the University of California, Oakland, Calif.

[21] Appl. No.: 09/302,047

[22] Filed: Apr. 29, 1999

[51] Int. Cl.[7] .......................... G01N 29/02; G01N 31/06; G01N 29/18

[52] U.S. Cl. ..................... 73/23.35; 73/23.42; 73/24.01; 73/24.06; 73/580

[58] Field of Search .............................. 73/23.35, 23.42, 73/23.2, 24.06, 597, 599, 596, 19.03, 24.01, 31.05, 580

[56] References Cited

U.S. PATENT DOCUMENTS

| | | | |
|---|---|---|---|
| 3,447,360 | 6/1969 | Laseter | 73/23.1 |
| 3,537,297 | 11/1970 | Loyd et al. | 73/23.1 |
| 3,608,276 | 9/1971 | Bloomer | 55/126 |
| 3,735,565 | 5/1973 | Gilby et al. | 55/197 |
| 3,772,909 | 11/1973 | Anderson | 73/23.1 |
| 3,847,546 | 11/1974 | Paul | 23/230 PC |
| 4,312,228 | 1/1982 | Wohltjen | 73/597 |
| 4,361,026 | 11/1982 | Muller et al. | 73/23 |
| 4,621,518 | 11/1986 | Gerdes | 73/29 |
| 4,895,017 | 1/1990 | Pyke et al. | 73/23 |
| 4,991,423 | 2/1991 | Poshemansky et al. | 73/23.35 |
| 5,012,668 | 5/1991 | Haworth | 73/24.06 |
| 5,076,094 | 12/1991 | Frye et al. | 73/19.03 |
| 5,239,483 | 8/1993 | Weir | 364/497 |
| 5,289,715 | 3/1994 | Staples et al. | 73/24.01 |
| 5,406,829 | 4/1995 | Ravel et al. | 73/24.01 |
| 5,583,281 | 12/1996 | Yu | 73/23.42 |

FOREIGN PATENT DOCUMENTS

| | | |
|---|---|---|
| 0921392 | 9/1999 | European Pat. Off. . |
| 4409053 | 9/1995 | Germany . |
| WO 86/04989 | 8/1986 | WIPO . |

OTHER PUBLICATIONS

Monitoring of $NH_3$ Gas by LB Polypyrrole–based SAW Sensor, M Penza et al., Sensors and Actuators B47 (1998), 218–224.

Development of a SAW Gas Sensor for Monitoring $SO_2$ Gas, Y. Lee et al., Sensors and Actuators A64 (1998), 173–178.

Enzymatic Assay of Acid Phosphatase and Microanalysis of $Cu^{2+}$ and $Ag^+$ With a SAW–Impedance Sensor, R. Wang et al., Enzyme and Microbial Technology 22:36–41, 1998.

SAW $NO_x$ Gas Sensor Using $WO_3$ Thin–Film Sensitive Coating, M. Penza et al., Sensors and Actuators B41 (1997), 31–36.

Studies on a Surface Acoustic Wave (SAW) Dosimeter Sensor for Organophosphorous Nerve Agents, M. Nieuwenhuizen et al., Sensors and Actuators B40 (1997), 167–173.

*Primary Examiner*—Hezron Williams
*Assistant Examiner*—J. David Wiggins
*Attorney, Agent, or Firm*—Lloyd E. Dakin; Alan H. Thompson; Christopher J. Horgan

[57] ABSTRACT

A system and method for preconcentrating, identifying, and quantifying chemical and biological substances is disclosed. An input valve directs a first volume of a sample gas to a surface acoustic wave (SAW) device. The SAW device preconcentrates and detects a mass of a substance within the sample gas. An output valve receives a second volume of the sample gas containing the preconcentrated substance from the SAW device and directs the second volume to a gas chromatograph (GC). The GC identifies the preconcentrated substance within the sample gas. A shunt valve exhausts a volume of the sample gas equal to the first volume minus the second volume away from the SAW device and the GC. The method of the present invention includes the steps of opening an input valve for passing a first volume of a sample gas to a SAW device; preconcentrating and detecting a mass of a substance within the sample gas using the SAW device; opening an output valve for passing a second volume of the sample gas containing the preconcentrated substance to a gas chromatograph (GC); and then identifying the preconcentrated substance within the sample gas using the GC.

28 Claims, 2 Drawing Sheets

SYSTEM AND METHOD FOR PRECONCENTRATING, IDENTIFYING, AND QUANTIFYING CHEMICAL AND BIOLOGICAL SUBSTANCES

CROSS-REFERENCE TO RELATED PATENT

This application relates to and incorporates by reference U.S. Pat. No. 5,583,281, entitled "Microminiature Gas Chromatograph," filed on Jul. 7, 1995, by inventor Conrad M. Yu. This related application is assigned to The Regents of the University of California, of Oakland, Calif.

The United States Government has rights in this invention pursuant to Contract No. W-7405-ENG-48 between the United States Department of Energy and the University of California for the operation of Lawrence Livermore National Laboratory.

BACKGROUND OF THE INVENTION

1. Field of the Invention

The present invention relates generally to gas chromatography, and more particularly to systems and methods for preconcentrating, identifying, and quantifying chemical and biological substances.

2. Discussion of Background Art

"Chromatography" is from the Greek word for "color writing." It is a method used in analytical chemistry to separate and identify the components of mixtures. The Russian botanist Mikhail S. Tswett (1872–1919) was the first (1903) to employ a general chromatographic technique. Partition chromatography was introduced in 1941, paper chromatography in 1944, and gas chromatography in 1952. A method of thin-layer chromatography was developed for general use in 1958. Since then, many chromatographic techniques have been developed that provide for specific needs, e.g., high performance, or pressure, liquid chromatography, gel permeation chromatography, ion chromatography, and concurrent chromatography. Prior art methods have emphasized both sensitivity and speed.

Column chromatography uses a vertical tube, or column, filled with a finely divided solid, a "stationary phase." A mixture of materials to be separated is placed at the top of the tube and is slowly washed down with a suitable liquid, or eluent, a "mobile phase." As the mixture dissolves, each molecule is transported in the flowing liquid and becomes adsorbed into the stationary solid. Each type of molecule spends a different amount of time in the liquid phase, depending on its tendency to be adsorbed. Thus each compound descends through the column at a different rate. The various compounds stratify over physical distance in the column, as in a parfait.

Mobile phases may be gases or liquids, and stationary phases are either liquids adsorbed on solid carriers or solids. When a liquid stationary phase is used, the process is called partition chromatography, since the mixture to be analyzed will be partitioned, or distributed, between the stationary liquid and a separate liquid mobile phase. Where the stationary phase is solid, the process is known as adsorption chromatography. The molecules of the mixture to be separated pass many times between the mobile and stationary phases at a rate that depends on the mobility of the molecules, the temperature, and the binding forces involved. The difference in the time that each type of molecule spends in the mobile phase leads to a difference in the transport velocity and to the separation of substances.

Commonly used adsorbents are silica gel and alumina, which are powdered into particles between 0.05 and 0.2 mm (0.002 to 0.08 in) in diameter for optimal flow. Stationary phases with very different properties can be obtained; and many different mixtures can be separated if a suitable adsorbent is chosen, and the powder is impregnated with a liquid. Stepwise, or fractional, elution involves eluting with liquids of increasing or decreasing polarities. The emerging liquid eluate can be collected automatically in small portions by a fraction collector. Each fraction is then analyzed separately. The eluate may then be passed through a spectrophotometer that measures the light absorption when a specific substance leaves a column. For the analysis of substances still in the column, the solid can be carefully pushed out of the column, cut into small sections, and treated.

In thin-layer chromatography (TLC), the stationary phase is a thin layer on a glass plate or plastic film. Typical thin layers comprise one of the usual adsorbents, such as silica gel or alumina made into a slurry and dried in a homogeneous layer on the glass plate. The mixture to be separated is first dissolved in a volatile solvent, and a small sample of this solution is placed on the thin layer. The solvent is then evaporated, and only the mixture to be separated remains in the form of a small spot. The plate is placed in an upright position in a jar. A carefully chosen developing solvent is then added to the bottom, the atmosphere in the jar is completely saturated with the vapor of the eluent, and the dish is closed. The liquid rises along the plate by capillarity. When it has risen 10–15 cm (4–6 in), in 10–20 minutes, the development is stopped and the plate is dried. Most chromatograms can be examined under ultraviolet light to locate the compounds. However, if the compounds are colorless, the plate is sprayed with a special reagent that colors the various compounds. Paper chromatography uses a stationary phase of water adsorbed on paper and a mobile phase of an organic liquid and is similar to thin-layer chromatography.

Gas chromatography includes gas-liquid chromatography (GLC) and the far less common gas-solid (GSC) method. The stationary phase is a liquid on a solid support, which is pressed into a narrow, coiled column 1.5–5 m (4–15 ft) in length. The mobile phase is an inert gas, usually nitrogen, hydrogen, helium, or argon, which is passed through a heated column. The sample mixture is injected into the column and immediately vaporizes. Its constituent substances separate and flow at different rates with the carrier gas. A detector is placed at the end of the column, which outputs a signal to a recorder in the form of a gas chromatogram having a series of detector maximums. Each peak is characteristic of a particular substance in the sample gas.

An important part of each gas chromatograph is its detector. Various types have been developed, including the katharometer, the flame ionization detector, and the electron capture detector. The flame ionization detector can detect a sample as small as $10^{-11}$ grams of material. The electron capture detector is as much as 100 times more sensitive than that. As such, gas chromatography has become an essential analytical tool in many chemical laboratories.

High performance liquid chromatography, or high pressure liquid chromatography (HPLC), is a refinement of standard column chromatography and has become, along with GLC, one of the two most commonly used separative techniques. In HPLC, the particles that carry the stationary liquid phase are uniformly very small, e.g., 0.01 mm/0.0004 in. Thus, the stationary phase presents a large surface area to the molecules of the sample in the mobile liquid phase. A resistance to input pressure by a column filled with such small particles is overcome with a high-pressure pump to drive the mobile liquid phase through the column in a reasonable time. HPLC offers high resolution and sensitivity. A column of 25-cm (9.8-in) length has an overall efficiency of 10,000 plates or individual separations. HPLC can resolve a raw urine sample into 200 individual components. Its extraordinary sensitivity can be used to detect a concentration of one part in one billion of the chemical aflotoxin, which is toxic to humans in food concentrations of as little as ten parts in one billion. More recent HPLC's use smaller diameter columns (3–5 cm/1.2–2 in) that increase the analytic speed and conserve expensive solvents. Some units can now perform analyses in one minute or less.

Gel permeation chromatography is based on the filtering or sieving action of the stationary phase. The stationary phase material is selected from a set of adsorbents that have pores of uniform size in the range of 20 to 200 nm. While moving down the column loaded with this type of adsorbent, a molecule dissolved in the mobile liquid phase will be excluded from the adsorbent if its size is greater than that of the pores. If the molecular size is smaller, the molecule will become entrapped. Intermediate-size molecules will permeate some pores and not others. The result is a separation based on molecular size, with the larger molecules separating out first and the smaller molecules last. This technique is used to separate and measure the molecular weight of polymers, proteins, and other biological substances of high molecular weight.

Making gas chromatographs smaller has been an objective in the prior art. Drew, et al., describe in U.S. Pat. No. 5,313,061, issued May 17, 1994, a miniaturized mass spectrometer system. A battery-operated portable unit is used in the field to analyze the atmosphere, water, soil, drugs, explosives and other substances. Such patent is incorporated herein by reference. Even though such a mass spectrometer system has been miniaturized, it is still quite large and not easily carried, e.g., as in a shirt pocket.

SAW devices, see Benes, E R; Groschl, R; Seifert, F; Pohl, A. "Comparison between BAW and SAW sensor principles," IEEE Transactions on Ultrasonics Ferroelectrics and Frequency Control," 1998 SEP, V45 N5:1314-1330, are used alone in direct measurement of total samples' weight which are condensed on the surface of the device. By using different boiling points of different chemical samples, different chemical samples can be identified.

Some laboratory systems use a GC in front of a SAW device, see Penza, M; Milella, E; Anisimkin, VI. "Monitoring of NH3 gas by LB Polypyrrole-Based SAW Sensor," in Sensors and Actuators B-Chemical, 1998 APR 30, V47 N1-3:218-224. Such a configuration, however, requires a very large sample size (more than several nano-grams). Since sample sizes in a hand-held GC are only about 1.5×10^(−3) nano-grams for PPM detection, the Penza reference has sensitivity of detection problems.

Because sample size used in Hand-Held GCs, discussed above, is much smaller than the minimum required by SAW detector, SAW detectors and GCs in the configuration described above are unworkable.

In response to the concerns discussed above, what is needed is a system and method for preconcentrating, identifying, and quantifying chemical and biological substances that overcomes the problems of the prior art.

SUMMARY OF THE INVENTION

The present invention is a system and method for preconcentrating, identifying, and quantifying chemical and biological substances. Within the system of the present invention, an input valve directs a first volume of a sample gas to a surface acoustic wave (SAW) device. The SAW device preconcentrates and detects a mass of a substance within the sample gas. An output valve receives a second volume of the sample gas containing the preconcentrated substance from the SAW device and directs the second volume to a gas chromatograph (GC). The GC identifies the preconcentrated substance within the sample gas. A shunt valve exhausts a volume of the sample gas equal to the first volume minus the second volume away from the SAW device and the GC.

The method of the present invention includes the steps of opening an input valve for passing a first volume of a sample gas to a SAW device; preconcentrating and detecting a mass of a substance within the sample gas using the SAW device; opening an output valve for passing a second volume of the sample gas containing the preconcentrated substance to a gas chromatograph (GC); and then identifying the preconcentrated substance within the sample gas using the GC.

The system and method of the present invention are particularly advantageous over the prior art because by placing the SAW device before the GC, a single hand-held device can sequentially characterize a mass and elemental composition of substances within various sample gasses. This arrangement also enables substances within the sample gas to be preconcentrated and thus increases an effective sensitivity of the GC.

These and other aspects of the invention will be recognized by those skilled in the art upon review of the detailed description, drawings, and claims set forth below.

DETAILED DESCRIPTION OF THE PREFERRED EMBODIMENT

Figure 1:
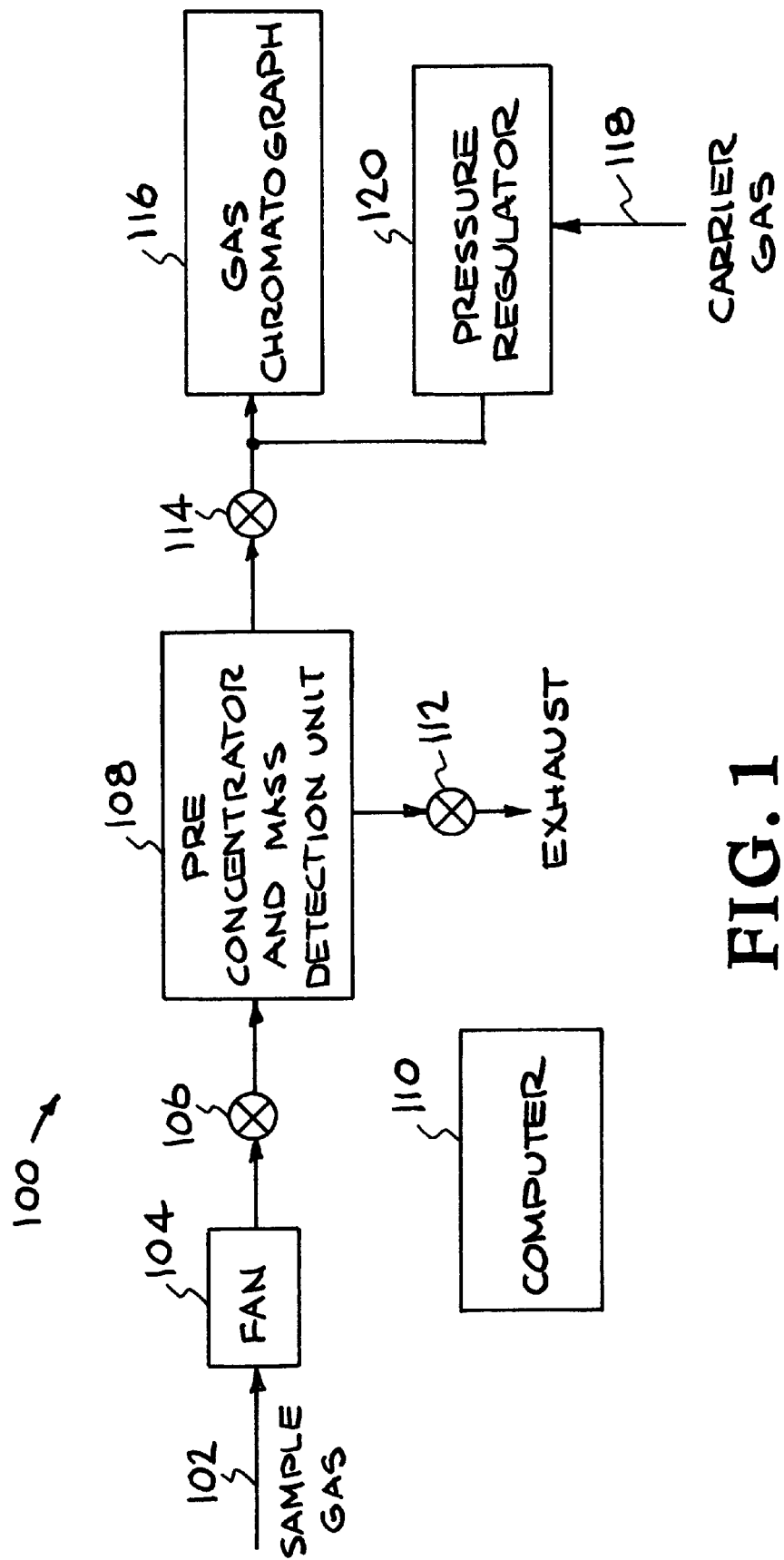
FIG. 1 is a block diagram of a system for preconcentrating, identifying, and quantifying chemical and biological substances.

FIG. 1 is a block diagram of a system 100 for preconcentrating, identifying, and quantifying chemical and biological substances, atomic elements, and/or molecules. A sample gas 102 containing chemical and/or biological substances to be identified is received by a fan 104. The fan 104 directs the sample gas to an input valve 106. The input valve 106 introduces the sample gas into a preconcentrator and mass detection unit 108 in response to control signals from a computer 110. The preconcentrator and mass detection unit 108 is preferably an enclosed retention chamber for containing the sample gas.

The preconcentrator and mass detection unit 108 contains a plurality of surface acoustic wave (SAW) devices which preconcentrate predetermined chemical and/or biological substances on the SAW devices and then detect a total mass of each substance. To effect preconcentration and mass detection, a relatively large volume of the sample gas, on the order of tens of cubic-centimeters, is pumped by the fan 104 through the preconcentrator and mass detection unit 108. The sample gas exits the preconcentrator and mass detection unit 108 through a shunt valve 112, which is kept open by the computer 110 during the preconcentration and mass detection step. The computer keeps an output valve 114, connecting the preconcentrator and mass detection unit 108 to a gas chromatograph (gas chromatograph) 116, closed during the preconcentration and mass detection step.

Once a predetermined amount of the sample gas is passed through the preconcentrator and mass detection unit 108, the computer closes the input valve 106 and the shunt valve 112. The computer 110 then processes data received from the SAW devices in the preconcentrator and mass detection unit 108 and records a total mass of substances within the sample gas which collected on each SAW device.

Next, the computer 110 pressurizes the preconcentrator and mass detection unit 108. When a predetermined pressure is reached, the computer 110 quickly opens and closes the output valve 114 which injects a relatively small amount, on an order of microliters, of preconcentrated sample gas 102 into a spiral gas chromatograph (gas chromatography column 116. The gas chromatograph 116 identifies the chemical and biological substances within the sample gas in parts per billion.

The gas chromatograph 116 is constructed according to the information provided in U.S. Pat. No. 5,575,929 entitled, "Method for Making Circular Tubular Channels with Two Silicon Wafers," by Conrad Yu, et al., and U.S. patent application Ser. No. 08/892,586 entitled "Micro-Miniature Gas Chromatograph Column Disposed in Silicon Wafers," by Conrad Yu and filed on Jul. 14, 1997, both of which are herein incorporated by reference.

Along with the sample gas 102, a carrier gas 118 is simultaneously injected into the gas chromatograph 116. The carrier gas 118 is typically an inert gas such as helium, nitrogen or hydrogen, which is directed to the gas chromatograph 116 through a pressure regulator 120. The pressure regulator 120 receives the carrier gas 118 at about 50 PSI. and regulated the gas down to about 20 PSI. The gas chromatograph 116 uses a thermal conductivity detector in a Whetstone Bridge based circuit to transduce the substances in the sample gas 102 into an output signal.

The computer 110 receives the output signal from the detector in the gas chromatograph 116 and uses a customized "Lab-View" software package to identify the substances in the sample gas 102. "Lab-View" is a software package manufactured by National Instruments Corp. of Austin, Tex., which is programmed to control and interpret data from the system 100. The "LabView" software uses a peak recognition comparison routing, which compares output signal peaks from the gas chromatograph 116 with a set of pre-stored "chemical signature standard" peaks to identify chemical and/or biological substances within the sample gas 102. These "chemical signature standards" are commercially available from a variety of well known manufactures.

As described above, the gas chromatograph 116 needs on the order of only a few micro-liters of the sample gas 102, while the preconcentrator and mass detection unit 108 requires on the order of several cubic centimeters of the sample gas 102. Furthermore, the gas chromatograph 116 will "flood" and thus generate inaccurate output signals if too much of the sample gas 102 is injected, while the preconcentrator and mass detection unit 108 will generate no or weak output signals if too little of the sample gas 102 is passed over the SAW devices. For these reasons, mass detection and substance identification are typically performed on at least two different machines. An advantage of the present invention is that both mass detection and substance identification are performed within one device having one sample gas 102 source. Positioning the preconcentrator and mass detection unit 108 before the gas chromatograph 116 enables this. Further, since the preconcentrator and mass detection unit 108 also acts as a preconcentrator, the gas chromatograph 116 can detect even more minute substances within the sample gas 102.

Preferably the system 100 is hand held, however the invention is also applicable to desktop and other systems.

Figure 2:
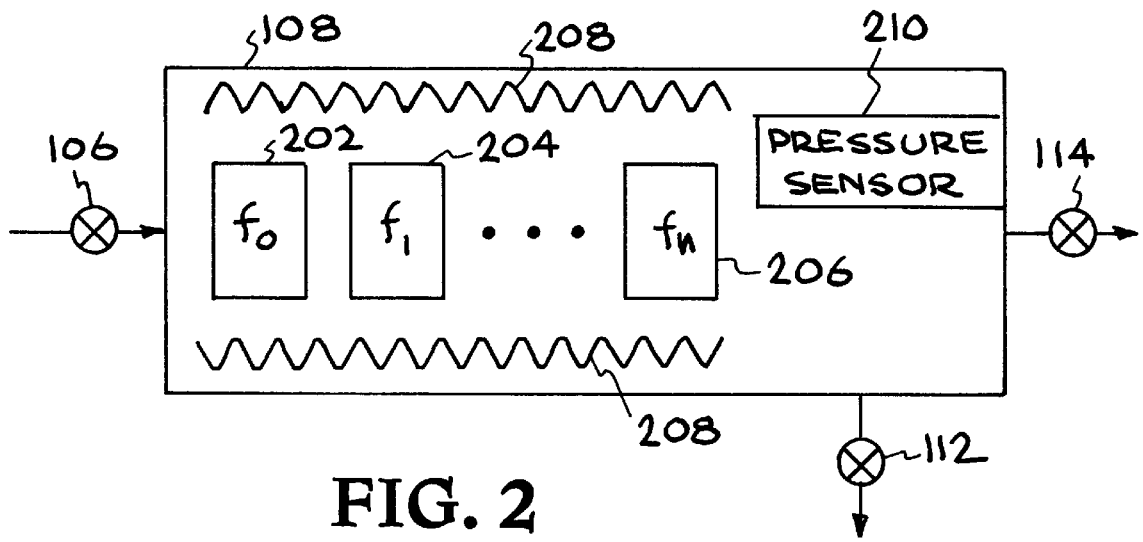
FIG. 2 is a block diagram of the preconcentrator and mass detection unit.

FIG. 2 is a block diagram of the preconcentrator and mass detection unit 108 of the present invention. The preconcentrator and mass detection unit 108 includes a set of piezoelectric quartz crystal surface acoustic wave (SAW) devices 202, 204, 206 each having predetermined resonant frequencies f0, f1, fn respectively. The resonant frequency of each SAW device 202, 204, 206 collects molecules having a mass responsive to the resonant frequency and repels other molecules. Depending upon chemicals and/or biological substances to be detected, different quartz crystals are inserted into the preconcentrator and mass detection unit 108. A mass of a complex substance may be determined using a different SAW device 202, 204, 206 for each molecular component of the substance. Preferably at least six different SAW devices 202, 204, 206 are used.

Figure 3:
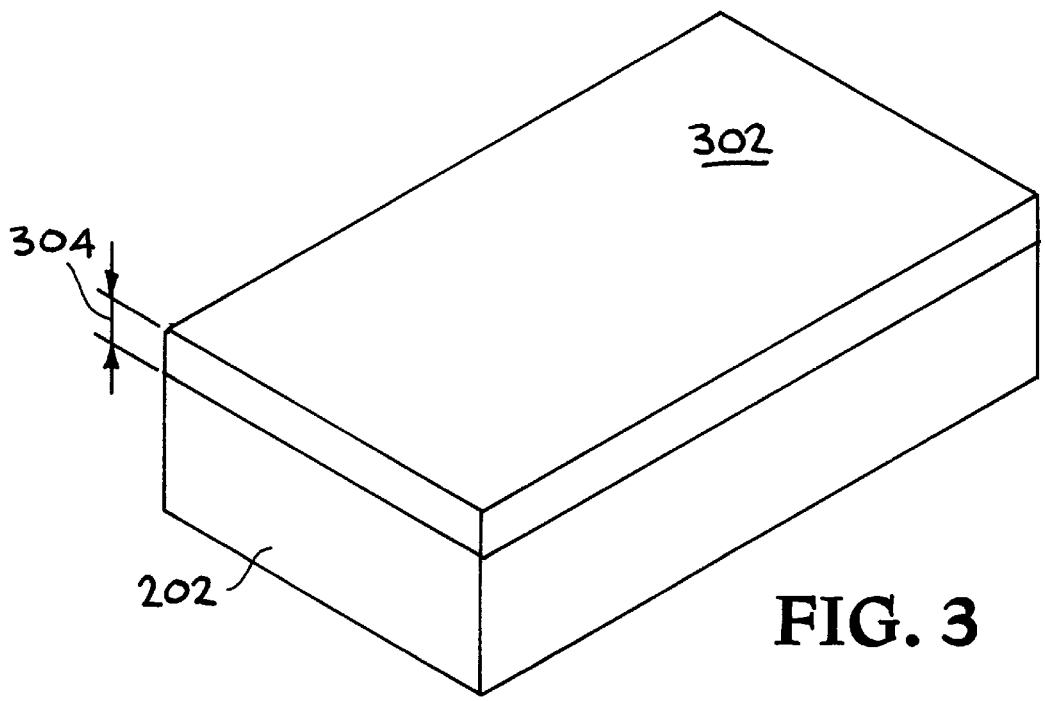
FIG. 3 is a block diagram of a surface acoustic wave device within the preconcentrator and mass detection unit.

FIG. 3 is a block diagram of the surface acoustic wave device 202 within the preconcentrator and mass detection unit 108. A polyamid coating 302 covers each SAW device 202 to further attract and retain selected molecular substances within the sample gas 102. Polyamid coatings are a subclass of organic, plastic, long-chain coatings. Application of polyamid coatings to a SAW device in order to better attract and retain various molecular masses is well known in the art. Depending upon a molecule to be attracted, a different polymer coating 302 is selected. Polyamid coating 302 thickness 304 is also adjusted, depending upon an amount of a substance to be captured and/or depending upon a size of a molecule within the substance to be captured. In general, thicker coatings are used to collect larger molecules and thinner coating are used to collect smaller molecules.

Referring back to FIG. 2, molecules within the sample gas 102 which are attracted to the resonant frequency of the SAW device and the polyamid coating, collect on SAW device and thereby slightly change the SAW device's vibrational frequency, which is monitored by the computer 110. The "LabView" software running on the computer 110 then calculates a total mass of the molecules collected from the sample gas 102 using this slight change in frequency information. Since these substances are collected, the preconcentrator and mass detection unit 108 also functions as a preconcentrator, enabling the gas chromatograph 116 to identify very minute traces of various substances than would otherwise be possible using only the gas chromatograph 116 by itself.

After this preconcentration step, the SAW devices must be out-gassed and injected into the gas chromatograph 116. This out-gassing also cleans the SAW devices in preparation for analysis of a next sample gas. Out-gassing is effected through use of ultraviolet filaments 208 which heat to the preconcentrator and mass detection unit 108. Heating also pressurizes the preconcentrator and mass detection unit 108 as monitored by a pressure sensor 210. This pressure aid injection of the preconcentrated substances into the gas chromatograph 116 once the output valve 114 is opened. During heating the input, shunt, and output valves 106, 112, and 114 are kept closed. The computer 110 then processes information from both the preconcentrator and mass detection unit 108 and the gas chromatograph 116 to provide a molecular and mass signature of the sample gas 102.

While the present invention has been described with reference to a preferred embodiment, those skilled in the art will recognize that various modifications may be made. Variations upon and modifications to the preferred embodiment are provided by the present invention, which is limited only by the following claims.

What is claimed is:

1. A system for characterizing chemical and biological substances comprising:
    a surface acoustic wave (SAW) device employed as a substance concentrator that is coupled to receive and detect a mass of a substance within a sample gas; and
    a gas chromatograph (GC), coupled to receive the sample gas with said substance mass therein from the SAW device after the substance concentration or mass detection has been completed, for identifying the substance within the sample gas.

2. The system of claim 1 further comprising:
    an input valve, coupled to the SAW device, for directing a first volume of the sample gas to the SAW device;
    an output valve, coupled between the SAW device and the GC, for directing a second volume of the sample gas from the SAW device to the GC; and
    a shunt valve, coupled to the SAW device, for exhausting a volume of the sample gas equal to the first volume minus the second volume.

3. The system of claim 2 further comprising:
    a retention chamber, coupled to the valves and enclosing the SAW device.

4. The system of claim 1 further comprising:
    a polyamid coating coupled to the SAW device, for aiding accumulation of the mass of the substance.

5. The system of claim 4 wherein the coating has a predetermined thickness based on the substance to be accumulated.

6. The system of claim 1 further comprising:
    a second SAW device, having a second resonant frequency, coupled to receive and detect a second mass from the sample gas.

7. The system of claim 2 further comprising:
    a computer, coupled to control operation of and receive data signals from the SAW device, the GC, and the valves.

8. The system of claim 2 further comprising:
    a heating filament, coupled to the SAW device, for causing the SAW device to out-gas the substance.

9. A system for concentrating chemical and biological substances comprising:
    a surface acoustic wave device employed as a substance concentrator, having
        a resonant frequency particular to a substance to be concentrated from a sample gas; and
        a polyamid coating that displays a chemical affinity or selective absorption towards said substance, the polyamid coating being particular to the substance to be concentrated from the sample gas; and electrical circuit means for monitoring any change in resonant frequency that is assumed proportional to an amount of said substance being accumulated onto said substance concentrator.

10. A method for characterizing chemical and biological substances, comprising the steps of:
    opening an input valve for passing a first volume of a sample gas to a surface acoustic wave (SAW) device;
    detecting a first mass of a substance within the sample gas using the SAW device where the SAW device displays a chemical affinity or selective absorption towards said substance;
    opening an output valve for passing a second volume of the sample gas containing a second mass of the substance to a gas chromatograph (GC) from the SAW device; and
    identifying the substance within the sample gas using the GC.

11. The method of claim 10 further comprising the step of:
    opening a shunt valve for exhausting a volume of the sample gas equal to the first volume minus the second volume.

12. The method of claim 10 further comprising the step of:
    coating the SAW device with a polyamid layer to aid accumulation of the mass of the substance within the sample gas.

13. The method of claim 12 wherein the coating step comprises the step of:
    coating the SAW device with a polyamid layer of a predetermined thickness based on the substance to be accumulated.

14. The method of claim 10 further comprising the steps of:
    passing the first volume of the sample gas to a second SAW device; and
    detecting a mass of a second substance within the sample gas using the second SAW device.

15. The method of claim 10 further comprising the step of:
    heating the SAW device in order to out-gas the substance.

16. A method for concentrating chemical and biological substances comprising the steps of:
    selecting a surface acoustic wave (SAW) device having a resonant frequency particular to a substance to be concentrated from a sample gas;
    coating the SAW device with a polyamid layer with a chemical affinity towards and that is particular to the substance to be concentrated from the sample gas; and
    passing the sample gas over the SAW device so that said particular substance is absorbed onto the polyamid layer of said SAW device, where the concentration of said particular substance is revealed electrically via a change in resonant frequency.

17. A system for characterizing chemical and biological substances, comprising:
    means for opening an input valve for passing a first volume of a sample gas to a surface acoustic wave (SAW) device;
    means for detecting a first mass of a substance within the sample gas using the SAW device where the SAW device displays a chemical affinity or selective absorption towards said substance;
    means for opening an output valve for passing a second volume of the sample gas containing a second mass of the substance from the SAW device to a gas chromatograph (GC); and
    means for identifying the substance within the sample gas using the GC.

18. The system of claim 17 further comprising:
    means for opening a shunt valve for exhausting a volume of the sample gas equal to the first volume minus the second volume.

19. The system of claim 17 further comprising:
    means for coating the SAW device with a polyamid layer to aid accumulation of the mass of the substance within the sample gas.

20. The system of claim 17 further comprising the step of:
means for heating the SAW device in order to out-gas the substance.

21. A system for concentrating chemical and biological substances comprising:
means for selecting a surface acoustic wave (SAW) device having a resonant frequency particular to a substance to be concentrated from a sample gas;
means for coating the SAW device with a polyamid layer with a chemical affinity towards and that is particular to the substance to be concentrated from the sample gas; and
means for passing the sample gas over the SAW device so that said particular substance is absorbed onto the polyamid layer of said SAW device, where the concentration of said particular substance is revealed electrically via a change in resonant frequency.

22. A method for concentrating chemical and biological substances comprising the steps of:
selecting a surface acoustic wave (SAW) device having a resonant frequency and having a polyamid layer coating with a chemical affinity towards and that is particular to a substance to be concentrated from a sample gas; and
passing the sample gas over the SAW device so that said particular substance is absorbed onto the polyamid layer of said SAW device, where the concentration of said particular substance is revealed electrically via a change in resonant frequency.

23. A system for concentrating chemical and biological substances comprising:
means for selecting a surface acoustic wave (SAW) device having a resonant frequency and a polyamid layer coating particular to a substance to be concentrated from a sample gas; and
means for passing the sample gas over the SAW device.

24. A system for characterizing chemical and biological substances comprising:
a first surface acoustive wave (SAW) device having a first resonant frequency coupled to receive and detect a first mass of a substance within a sample gas due to the SAW device displaying a chemical affinity or selective absorption towards said substance;
a second SAW device, having a second resonant frequency, coupled to receive and detect a second mass of the substance from the sample gas; and
a gas chromatograph (GC) coupled to receive the sample gas from the first or second SAW device, for identifying the substance within the sample gas.

25. A method for characterizing chemical and biological substances, comprising the steps of:
opening an input valve for passing a first volume of a sample gas to a surface acoustic wave (SAW) device;
detecting a mass of a first substance within the sample gas using the SAW device where the SAW device displays a chemical affinity or selective absorption towards said substance;
passing the first volume of the sample gas to a second SAW device;
detecting a mass of a second substance within the sample gas using the second SAW device;
opening an output valve for passing a second volume of the sample gas containing said first and second substances to a gas chromatograph (GC); and
identifying the type of first and second substance within the sample gas using the GC.

26. A system for concentrating and identifying chemical and biological substances comprising:
a plurality of surface acoustic wave devices (SAW) coupled to receive and detect a mass of a substance within a sample gas, each said SAW having
a resonant frequency particular to a substance to be concentrated from a sample gas; and
a polyamid coating which displays a chemical affinity or selective absorption towards said substance, the polyamid coating being particular to the substance to be concentrated from the sample gas; and
a gas chromatograph coupled to receive the sample gas from the SAW devices to identify the substance within the sample gas.

27. A method for concentrating and identifying chemical and biological substances comprising the steps of:
selecting one of a plurality of surface acoustic wave (SAW) devices having a resonant frequency and having a polyamid layer with a chemical affinity towards and that is particular to a substance to be concentrated from a sample gas;
passing a first volume of the sample gas over the selected SAW device so that said particular substance is absorbed onto the polyamid layer of said SAW device, where the concentration of said particular substance is revealed electrically via a change in resonant frequency; and
opening an output valve for passing a second volume of the sample gas to a gas chromatograph from the SAW devices.

28. A system for concentrating and indentifying chemical and biological substances comprising:
means for selecting one of a plurality of surface acoustic wave (SAW) devices having a resonant frequency and having a polyamid layer coating with a chemical affinity towards and that is particular to a substance to be concentrated from a sample gas;
means for passing a first volume of the sample gas over the selected SAW device so that said particular substance is absorbed onto the polyamid layer of said SAW device, where the concentration of said particular substance is revealed electrically via a change in resonant frequency; and
opening an output valve for passing a second volume of the sample gas to a gas chromatograph from the SAW devices.

* * * * *